United States Patent [19]

Gaspard

[11] Patent Number: 5,025,219
[45] Date of Patent: Jun. 18, 1991

[54] APPARATUS AND METHOD CONTINUOUS MEASUREMENT OF THE ELECTRICAL CONDUCTIVITY OF LIQUID MEDIA IN A DYNAMIC CELL

[75] Inventor: Jean R. Gaspard, St. Jean De Maurienne, France

[73] Assignee: Pechiney Recherche, Paris, France

[21] Appl. No.: 409,058

[22] Filed: Sep. 19, 1989

[30] Foreign Application Priority Data

Sep. 20, 1988 [FR] France ................. 88 12704

[51] Int. Cl.$^5$ ........................................... G01N 27/02
[52] U.S. Cl. .................... 324/447; 204/1 T; 324/439; 324/444
[58] Field of Search ............... 324/438, 439, 442, 444, 324/446, 447; 204/1 T, 406

[56] References Cited

U.S. PATENT DOCUMENTS

| | | | |
|---|---|---|---|
| 2,698,539 | 1/1955 | Gridel et al. | 324/447 X |
| 3,365,376 | 1/1968 | Weyland | 324/447 X |
| 4,769,607 | 9/1988 | Bauman et al. | 324/439 X |

Primary Examiner—Reinhard J. Eisenzopf
Assistant Examiner—Robert W. Mueller
Attorney, Agent, or Firm—Dennison, Meserole, Pollack & Scheiner

[57] ABSTRACT

An apparatus for providing a precise, continuous, and dynamic measurement of the electrical resistivity of a liquid medium. A dynamic measurement cell is provided with at least one conduit of electrically insulating material in which a conductive electrode slides with a motion of given amplitude. The lower portion of the conduit is calibrated over a length equal to at least the given amplitude, and has a known cross-section. The cell is immersed in a crucible containing the liquid medium for test at constant temperature to monitor various electric parameters. The monitoring system provides devices for controlling, adjusting, and measuring the amplitude and speed of the displacement of the electrode; measuring and adjusting the depth of immersion of the electrodes; and, measuring the variation, in ohmic resistance, of the cell as a function of the displacement of the electrodes. The conductivity is determined by an equation proportional to the ratio of the change in amplitude to the change in resistance.

18 Claims, 6 Drawing Sheets

SEC. A-A

APPARATUS AND METHOD CONTINUOUS MEASUREMENT OF THE ELECTRICAL CONDUCTIVITY OF LIQUID MEDIA IN A DYNAMIC CELL

FIELD OF THE INVENTION

The invention relates to an apparatus and a method of precise continuous measurement in a dynamic cell of the electrical conductivity o of liquid media, either in solution or in the pyrogenic phase, in a range of temperatures that can extend from cryogenic temperatures to approximately 2000° C., and more particularly between ambient temperature and approximately 1000° C. It is the result of work performed in the Department of Materials Physics of the University of Lyon, Laboratory associated with the CNRS, No. UA 172.

It may apply in particular to the molten (mineral or organic) salts used among others in the processes for obtaining metals such as aluminum, magnesium, sodium, lithium, titanium, and rare earth metals by electrolysis, but this listing is not limiting.

It also applies to the precise measurement cf conductivity of certain molten metals (such as alkali metals), aluminum, magnesium and pyrogenic media comprising mixtures of salt and metal, such as mixtures of potassium and potassium chloride. It is particularly well suited to tracking the development over time of the conductivity of a liquid or molten medium as a function of various internal and/or external parameters.

STATE OF THE ART

The precise, continuous measurement of the conductivity of liquids and its development over time is a delicate operation, above all when aggressive media such as mineral salts or molten slags are involved, at temperatures which may be between several hundred and 1000° C. and even far beyond that.

In the literature, numerous measuring instruments have been described which are all characterized by the use of static cells with a fixed k constant, that is, where the electrodes are disposed in a fixed manner with respect to both the measurement cell and the liquid tested. The difficulty with this system is that it is difficult to separate the resistance of the liquid from the parasitic resistances of the system. If these parasitic resistances develop uncontrollably, then the actual conductivity of the liquid cannot be determined. In that case, the solution to the problem comprises making a statistical analysis of a large number of results, and calibrating the cell in order to determine k.

The measuring methods most often used at present and the apparatus with which they are associated are essentially as follows:

The impedence measuring bridge, a precise means with which the actual impedences R and complex impedences Z can be balanced, but it is impossible to use for continuous measurement, or for measuring a developing conductivity.

Impedometry, generally based on a measurement of the measuring current phase displacement with respect to the voltage. The most sophisticated equipment of this kind enables obtaining the values for dynamic resistance R, reactance X and phase displacement $\phi$. The performance of such equipment is often limited by the inadequate level of the signal-to-noise ratio and by the inadequate separation between R and X.

Synchronous detection methods are little used, because they require relatively sophisticated signal processing means. Nevertheless, because they have an excellent signal-to-noise ratio, they make it possible to attain high measurement precision and above all excellent separation between the actual and imaginary terms R and X, respectively, and it is this last method upon which the present invention is based.

SUBJECT OF THE INVENTION

A first subject of the invention is an apparatus for precise, continuous measurement of the resistivity $\sigma$ of a liquid and its development over time, at a temperature T which may be between low temperatures and approximately 2000° C., including in combination:

a dynamic measurement cell 2 provided with at least one conduit 5 of electrically insulating material, in which a conductive electrode 6 can slide by an alternating periodic motion of amplitude $\Delta l$, the lower portion 5A of the conduit being calibrated over a length equal to at least $\Delta l$ and having a cross section s, said cell 2 being immersed in a crucible 3 containing the liquid L;

a generator 22 of periodic current of frequency f, connected in series with the cell 2 that it supplies at an effective intensity i;

a device 10 for controlling, adjusting and measuring the amplitude of the phase displacement of each electrode 6;

a means 8 for measuring and adjusting the depth to which each conduit or group conduits 5A is immersed in the liquid L;

a device for adjusting and measuring the speed of displacement $\Delta l / \Delta t$ of the electrode 6 in the conduit 5A;

a means of measuring the variation in impedance and extracting the ohmic resistance R of the cell as a function of the displacement of each electrode $\Delta R / \Delta l$, on the basis of the voltage u at the terminals of the cell and the intensity i penetrating it, by synchronous detection;

the value of the conductivity $\sigma$ of the liquid L is deduced, as follows:

$$\sigma = \frac{n \cdot \Delta l}{s \cdot \Delta R}$$

where n is the number of electrodes 6 of the cell 2 and s is the cross section of the conduit 5A.

The apparatus further includes at least one means 9 for measuring and optionally adjusting the temperature, disposed at the level of the conduits 5A in proximity with the interface between the electrode 6 and bath L; the positioning of this means is preferably synchronized with that of the electrodes 6.

The apparatus that is the subject of the invention may include a single electrode 6, with the reverse current being effected either via an auxiliary fixed electrode, or a conductive crucible 3, but in general it includes two electrodes 6 that are movable in two adjacent, parallel conduits 5. It may also have more than two electrodes, which are even or odd in number.

A second subject of the invention is a method of precise, continuous measurement of the conductivity of a liquid cryogenic medium performed with the apparatus that is the first subject of the invention, and comprising:

sending a periodic current, which is preferably perfectly symmetrical, of frequency f and effective intensity i, through said cell, the electrodes 6 of which are excited by an alternating periodic motion of amplitude 1;

measuring the voltage u at the terminals of the cell;

processing these signals u and i by synchronous detection to obtain the value of the ohmic resistance R of the cell, which is the outcome of the in-phase ratio u/i;

determining $\sigma$ by applying the ratio $$\sigma = n \cdot \Delta l / s \cdot \Delta R,$$

where n is the number of electrodes of the cell, $\Delta l$ is the amplitude of the motion of the electrode in the conduit 5A, and s is the cross section of the conduit 5A.

DESCRIPTION OF THE INVENTION

FIGS. 1-8 illustrate the invention.

FIG. 1, in vertical section, shows the following: on the left in the portion 1A, the entire measurement cell that is the subject of the invention, and on the right 1B, the detail on a larger scale of the conduits and electrodes, and also, at 1C, a cross section taken along the line AA.

Figure 1A:
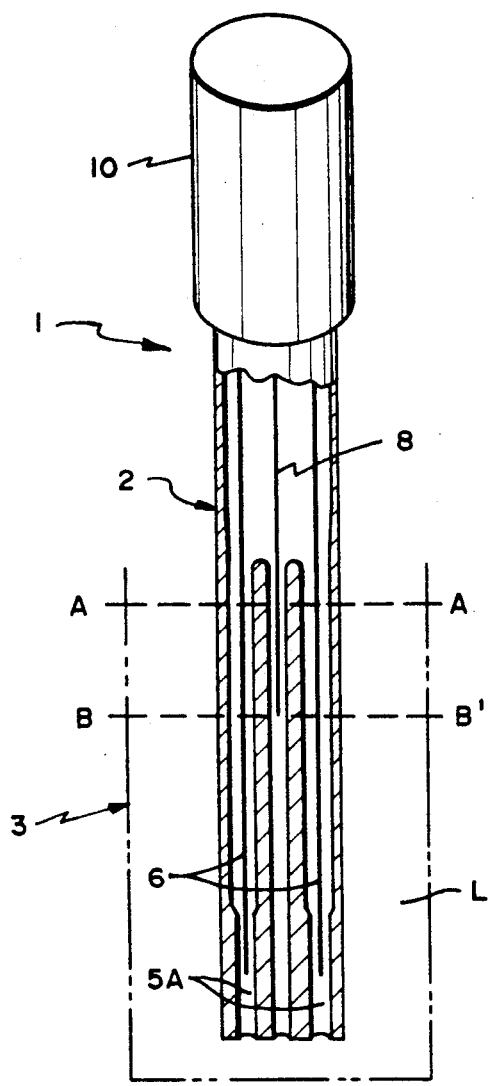
Figure 1B:
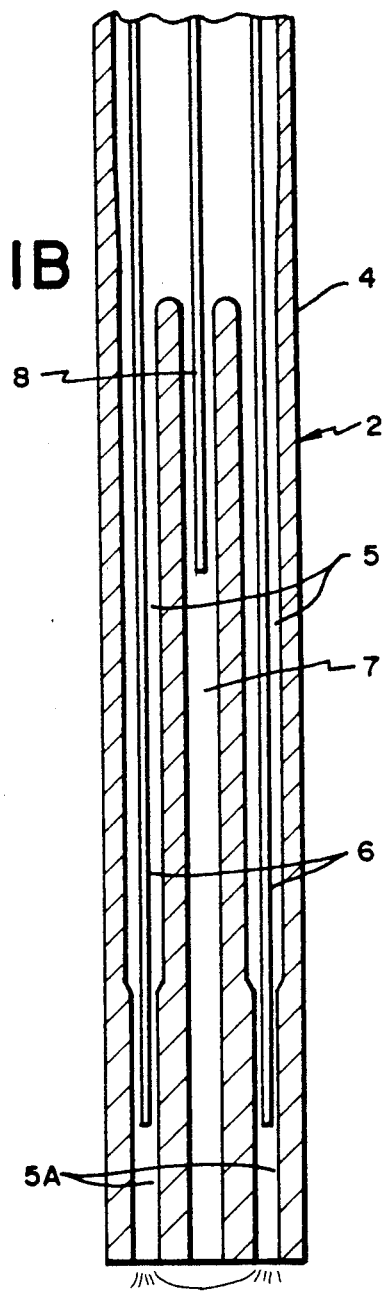
Figure 1C:
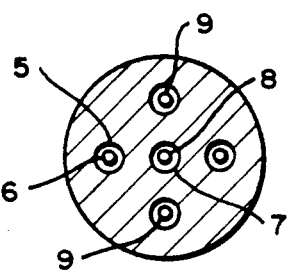

In the entire description that follows, "the liquid" (reference letter L in the drawings) designates the liquid or molten media: an aqueous solution or a simple or complex pyrogenic medium, in which the measurement electrodes are immersed and for which the measurements of electrical resistance are proposed to be made. Similarly, "the cell" (reference mark 1 in the drawings) designates the entire apparatus (electrodes and accessories) immersed in "the liquid", the electrical resistance of which is measured, and which comprises a dynamic cell.

DESCRIPTION OF THE MEASUREMENT APPARATUS

The measurement cell 1 includes one main element, which is the measurement device 2 per se associated with a device 10 for automatic control, or slaving, of the position of the electrodes.

The measurement device 2 comprises a tube 4 of electrically insulating material, selected for its resistance both to temperature and to the nature of the medium in which it functions, examples being glass, silicon dioxide, and ceramic. It is immersed in the liquid contained for example in the crucible 3, which is represented simply by its outline in dotted lines, up to a level represented by the horizontal line BB'. The tube 4 includes at least one conduit 5, parallel to the axis of the tube (in the case shown there are two conduits 5), this conduit being calibrated and having a known, constant cross section s at least in its lower portion 5A, which corresponds to the measurement zone scanned by the electrodes, while the upper portion, which is not directly involved in the measurement, may have a substantially larger cross section. Inserted into each conduit 5 is a measuring electrode 6, which can slide freely in this conduit. This electrode is of material that is a good conductor, preferably metal, and must comprise a metal resistant to the liquid L under the conditions of use, such as tungsten, molybdenum, tantalum, nickel or platinum depending on the case. It may also comprise a conductive ceramic, such as titanium diboride, tantalum carbide, or tin dioxide, these examples not comprising any limitation of the invention.

The tube 4 also includes a supplementary conduit 7, in which a movable electrode 8 is disposed that is intended for measuring (and adjusting) the depth of immersion of the cell in the liquid that is the subject of the measurement.

One or two further conduits 9 enable the disposition of one or two thermocouples at the height desired, in order to monitor and as applicable adjust the temperature of the liquid in which work is done. The position of the thermocouples is preferably slaved to the position of the electrodes, such that at any moment the temperature measurement is indeed performed in proximity with the electrode/bath interface. In the case of highly aggressive liquids, the housings 9 of the thermocouples are stoppered in their lower portion.

The upper portion of the device 2 includes an automatic control means 10 for the electrodes which are subjected to a vertical alternating motion, the amplitude 1 and the speed $\Delta l / \Delta t$ of which are predetermined and adjustable. It also includes a means for automatic control of the depth of immersion of the cell, comprising a differential amplifier connected to the electrode 8, which translates the position of this electrode when it comes into contact with the liquid into an electrical signal.

Figure 2:
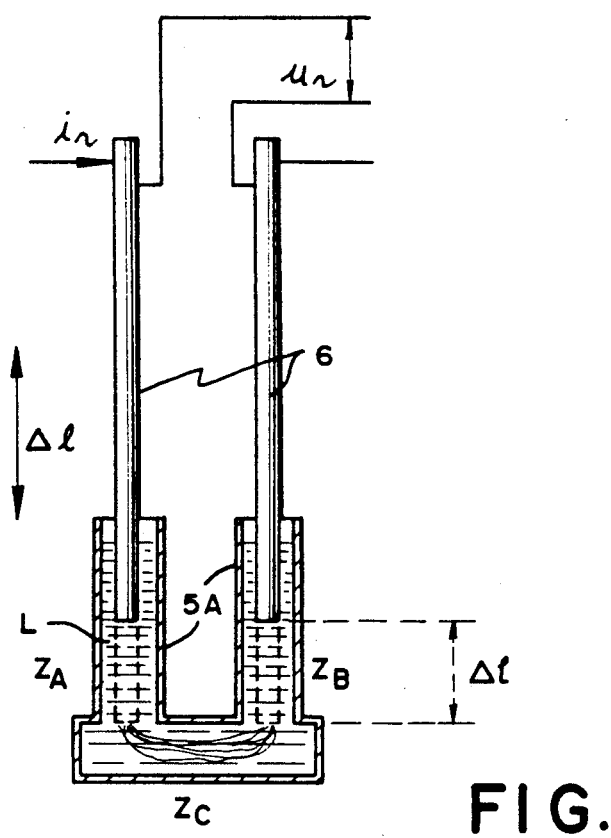
FIG. 2 is a schematic diagram showing the principle on which the measurement is based.

The principle on which the measurement method is based is schematically shown in FIG. 2: The alternating motion of the electrodes 6 in the calibrated conduits 5A, having an amplitude 1, engenders in each conduit a corresponding variation of the impedance equal to Za for one conduit and Zb for the other conduit. If the electrodes and conduits are properly calibrated, Za and Zb are substantially equal. Hence a variation Za+Zb corresponds to a variation in amplitude $\Delta l$, and the variation Za +Zb can be assimilated to 2Za without risk of major error. Thus the resistivity Zc of the liquid located between the ends of the two conduits, and all the other resistances of the system, do not come into play.

Figure 3:
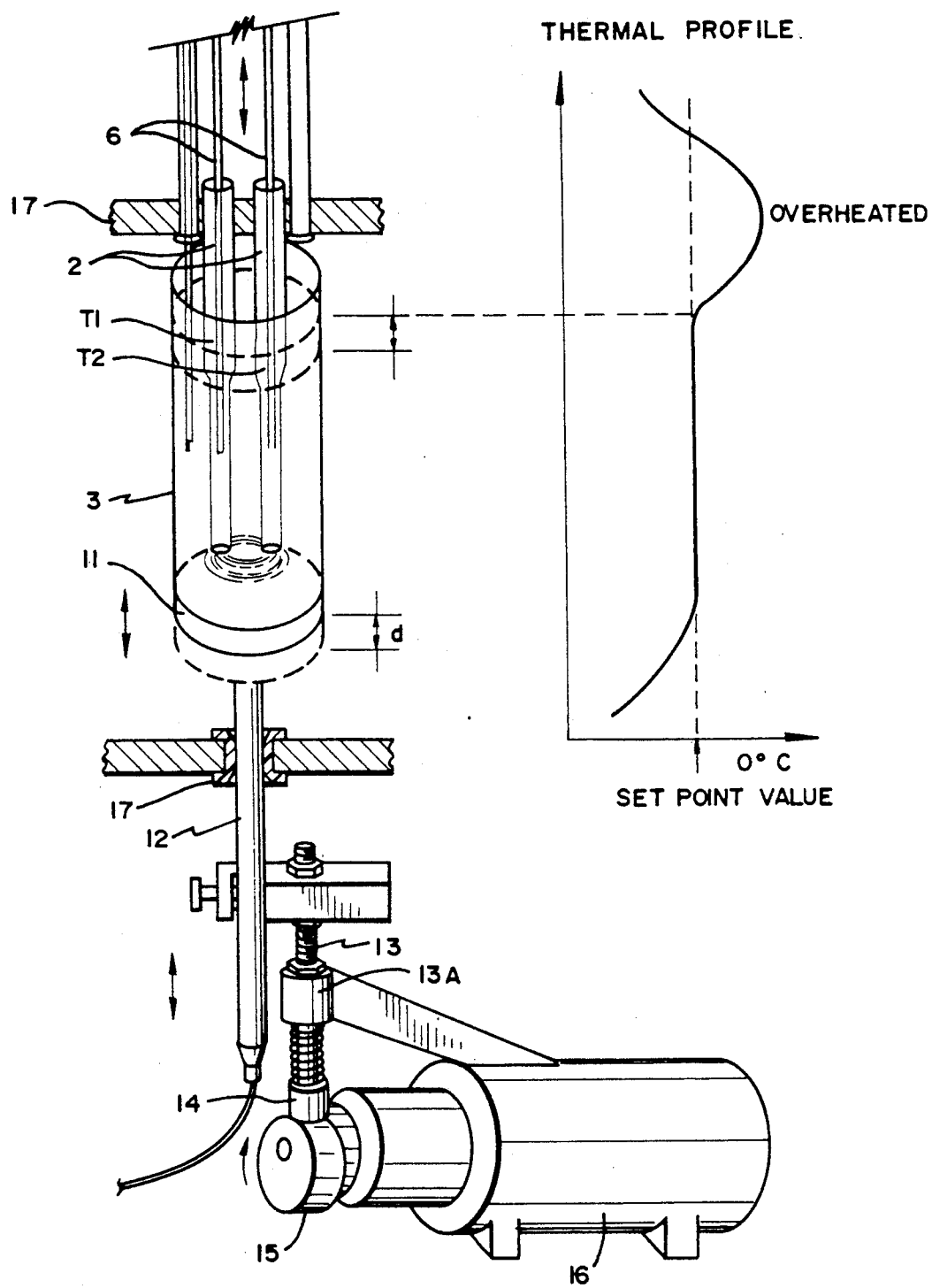
FIG. 3 shows the mechanical apparatus that assures the motion of the, crucible containing the liquid medium in such a manner as to assure and maintain its homogeneity.

A mechanical system makes it possible to assure a certain agitation of the liquid in the crucible 3, with a view to assuring its homogeneity; it is shown in detail in FIG. 3, in a particular embodiment, which comprises merely a non-limiting example:

The bottom 11 of the crucible 3 of the measurement cell is supported on a rigid rod 12 coupled to a threaded rod 13 of adjustable length, the lower portion 14 of the latter rod comprising a cam that cooperates with an eccentric element 15 the rotation of which is controlled by a rack-geared motor 16 of adjustable speed. Its rotational speed may be adjusted, for example, between 0.1 and 10 revolutions per second. The amplitude a of this motion is adjustable, for example between 0.2 and 30 mm.

This motion of the crucible creates a kind of flux and reflux of the liquid in the conduits, which assures the homogeneity of the liquid being measured and eliminates any risk of thermal gradient, concentration gradient and polarization of the electrodes in the liquid contained in the conduits 5A.

As a variant, it is possible to obtain agitation of the liquid by rotating the crucible 3 slowly or via a mechanical vibration of adjustable amplitude and speed.

When the cell 2 is disposed in an oven at elevated temperature, the entire mechanical portion (12-16) is disposed outside the oven, which is penetrated by the rod 12 via at least one gasket 17 of suitably selected material, such as fluorocarbon polymer, or expanded and recompressed graphite.

In the ensuing description, the hypothesis applied is the one in which the cell contains two electrodes disposed in the conduits of a tube of insulating material, as is most often the case.

Further embodiments are possible without departing from the scope of the invention.

In a first variant (which appears in FIG. 3), each electrode 6 is placed in a separate insulating tube, the two tubes being fixed to a common support 17' placed in the upper portion of the cell; this support 17' also serves to position the clad thermocouple or thermocouples 9 and the electrode 8 for measuring the depth of immersion.

It is also possible to use only a single measurement electrode, with the reverse current taking place then via the crucible 3 that contains the liquid L, and which crucible must then be of a current conducting material, or via a fixed auxiliary electrode. The system with two electrodes, as shown in the drawings, nevertheless has the advantage of feeding back the lines of measurement current between the two electrodes 6 at the ends of the tubes 5, which eliminates perturbation due to the walls and bottom of the crucible.

In another embodiment of the invention, more than two electrodes, of even or odd number, are used; these electrode/conduit systems form "unit cells" having k constants that are identical to or different from one another.

One way to proceed comprises associating two pairs of electrodes and conduits, that is, electrodes 6A-6B and 6C-6D having an equal or different constant k. If the constants k of the two pairs are equal, then by performing measurement alternatingly for one or the other pair, a means of verification that there is no difference between the results of measurement is available. Nevertheless, it is more worthwhile to introduce a difference between the two pairs, which may for example bear upon the nature of the conductive metal or compound comprising the electrodes, or upon the constant k, by using conduits 5A of different diameter for each pair, with the diameter and nature of the electrodes remaining identical; consequently a different free space is available between the surface of each electrode and the inside wall of the conduits 5A. In that case it is possible to detect any hydrodynamic effects in the conduits 5A as a function of the viscosity of the liquid L or the mass of the liquid in question.

Figure 4:
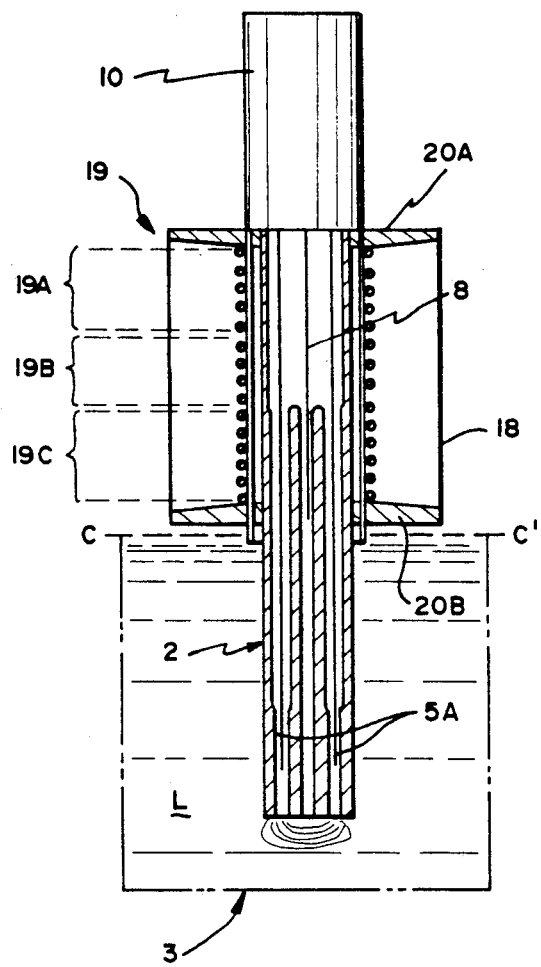
FIG. 4 shows the measurement cell disposed in a thermostatic oven for operation at elevated temperatures on metals or slags or molten salts, for example. The lower portion is immersed in the molten medium for which the measurements are made.

FIG. 4 shows an embodiment of the invention adapted for measurement at elevated temperatures.

The cell is immersed directly in the liquid up to a level marked by the horizontal line CC'. This immersion is adjusted and automatically controlled by the slaving device 10 connected to the movable electrode 8. To obtain elevated measurement precision, it is indispensible to reduce the thermal gradient over the entire height of the cell. To do so, the upper portion, which is not immersed in the liquid, is surrounded by an electric oven 18, the heating resistors 19 of which may preferably be separated into two or three groups 19A, 19B, 19C, with the primary adjustment bearing on the central group (19B in the case shown) functioning as a "master", while the two groups 19A and 19C are adjusted as "slaves", by a well-known method. Two thermal screens 20A, 20B monitor the flows of heat in the direction of the slaving system and the measuring zone.

This apparatus is particularly well suited to direct measurement of the conductivity of the electrolyte in industrial tanks, for example for the production of metals such as aluminum, sodium, lithium, magnesium, or rare earth metals, by pyrogenic electrolysis.

Figure 5:
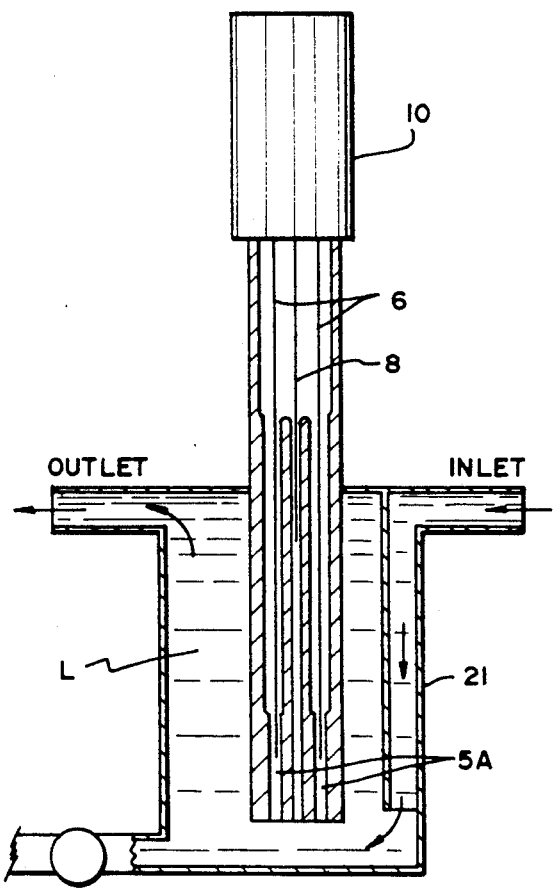
FIG. 5 shows an application to measurement of the conductivity of a circulating liquid.

FIG. 5 shows a variant embodiment in which the measurement cell is placed in an isothermic container 21 in which the liquid, the conductivity of which is to be measured, circulates. It may function continuously, in once-through fashion, or semicontinuously for successive volumes of liquid.

To proceed to measurement of volatile or oxidizable liquids, the measurement cell is placed in a sealed container E in such a way that work can be done at an inert gas pressure that may attain 0.5 MPa, for example, or prior to melting of the electrolyte, in a vacuum that may attain 1 Pa. The sealing means are conventional and are not part of the invention, As a variant, the crucible/cell assembly is disposed in a container E under excess pressure, contained in an oven having five distinct heating zones, which assures overheating above the liquid/gas interface, in such a way as to prevent the escape of volatile ingredients from inversion of the flow of metal vapors (FIG. 3, thermal profile).

Further improvements may also increase the precision of measurement, which is the case for following:

slaving between the speed of displacement of the electrodes and the integration of the output signal as a function of the scanning frequency and the size (sensitivity) selected for the measurement apparatus;

the slaving between the temperature profile determined along the conduits (FIG. 3) and adjusting the various zones of the oven.

B - DESCRIPTION OF THE SIGNAL PROCESSING APPARATUS AND TECHNIQUE

The measurement of electrical resistance R of the cell is performed on the basis of the method known as synchronous detection.

The principle of this method will be briefly recalled: The measurement current i, the frequency of which is adjustable, passes through the cell. The voltage drop u is measured at the terminals of the cell and the intensity i that passes through it is measured at the terminals of a non-reactive precision resistor 23B having a resistance of $1 \Omega \pm 10^{-5} \Omega$. Hence $u/i = R$, the resistance of the liquid in the conduits of cross section s.

The conductance $\sigma$ is deduced from the ratio of the pairs of measured magnitudes: $\Delta l$ and $\Delta R$; this ratio equals $2 \cdot \Delta l / \Delta R \cdot s$, in the case of a two-electrode system.

To be able to state that Z (as measured) = R, the formula $Z = R + jX$ must be used to extract the value of R, the real portion of the complex impedance Z. The value of R is deduced directly from the ratio u/i, strictly on the condition that u and i are measured rigorously in phase. This is the primary role of the synchronous detection.

Figure 6:
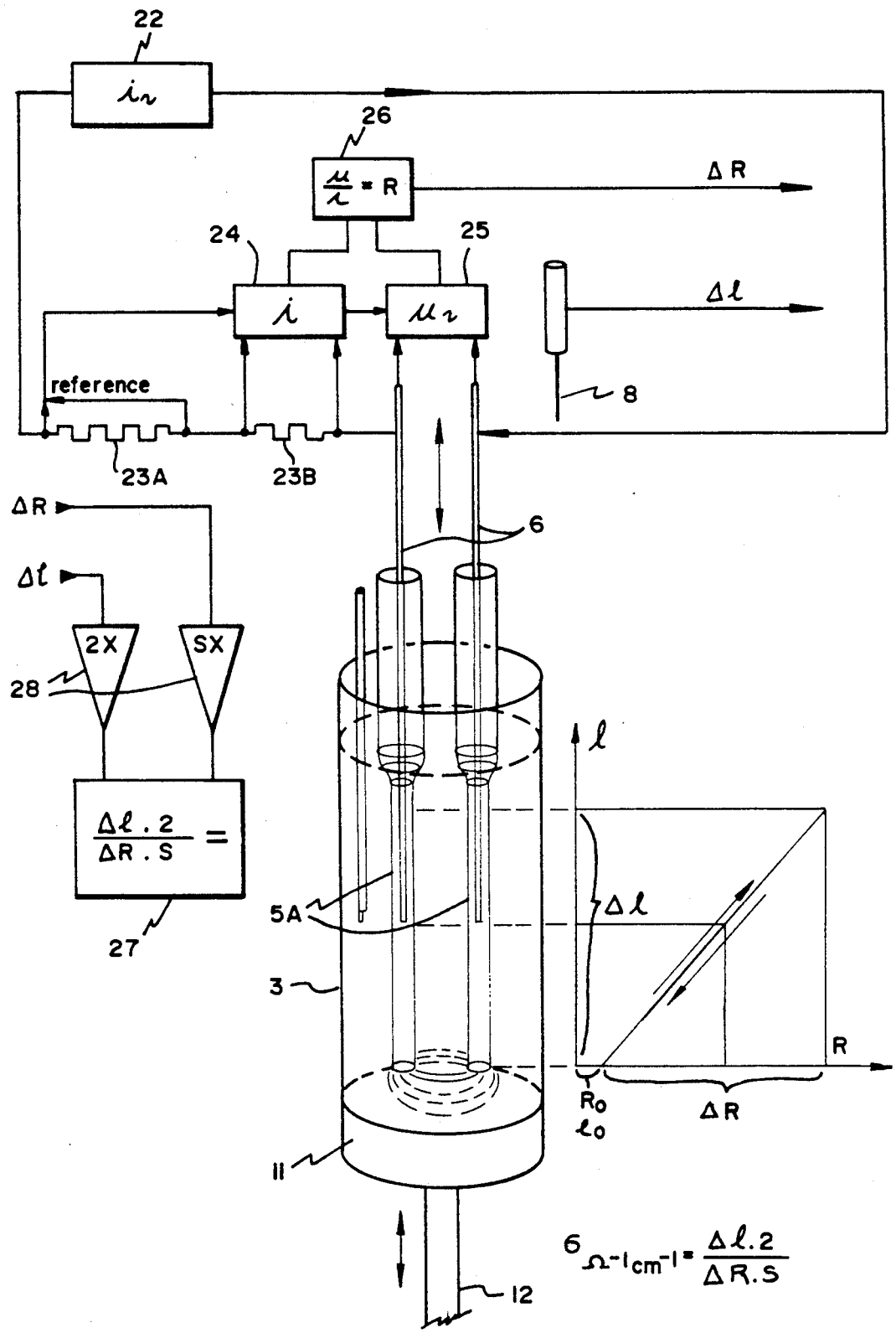
FIG. 6 illustrates the general principle of sampling and analysis of the signals in the measurement cell.
Figure 7:
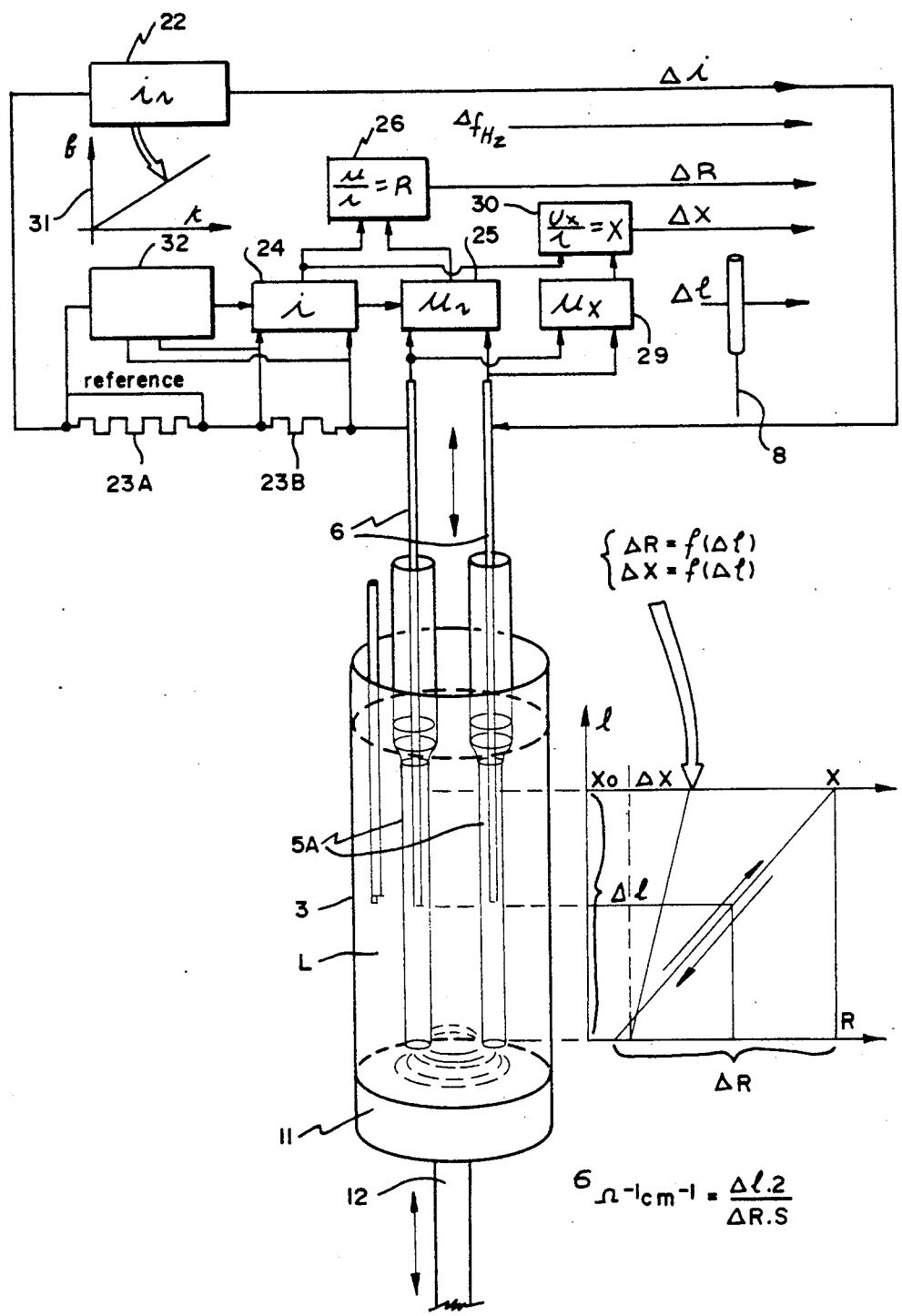
FIG. 7 shows a variant of the signal processing system with which a very high number of data can be obtained based on the data picked up, in particular the reactance of the cell.

To do this, the measurement chain includes the following devices (see FIG. 6):

a generator 22 of sinusoidal intensity i supplying a circuit including two precision resistors 23A, 23H, disposed in series with the cell; the generator 22 used may furnish a periodic, generally sinusoidal current at a frequency f between 1 and $10^5$ Hertz at an effective intensity between 10 $\mu$A and 1A. It is also possible to superimpose a continuous polarization that is adjustable between 1 V and 10V.

two synchronous detectors 24, 25, fixed or the current i (yielding the phase reference), respectively measure the values of the effective intensity i at the terminals of the resistor 23B and of the voltage u at the terminals of the cell; these two detectors 24, 25 furnish the following, respectively: a continuous image signal of the current i in constant phase relation with the reference signal, and a continuous image signal of the voltage u measured at the terminals of the cell in phase with the current i.

These synchronous detected image values of u and i make it possible, by using a precision ratiometer 26, to track the development of $\Delta R$ ($= \Delta u / \Delta i$ in phase) as a function of the variation $\Delta l$ of the position of the slaved electrodes 6.

A second precision ratiometer 27 makes it possible to obtain the conductivity $\sigma$ directly from the values of R and 1, which are introduced after amplification in the amplifiers 28 into each of the input routes of the ratiometer 27, which furnishes the value $\sigma = \Delta ln / \Delta R \cdot s$, where $\Delta l$ is the amplitude of the motion of the electrodes 6; n is the number of electrodes, hence 1 or 2, or more; R is the resistance; and s is the cross section of the tube 5 in the calibrated zone 5A.

Simultaneously, conventional measuring instruments display and preferably record the conditions under which the measurements are performed: temperature of the liquid; possible pressure of the insert gas in the container holding the cell and crucible assembly, if the measurement conditions require it; frequency and wave shape of the current; composition of the liquid, if it comprises a mixture; and so forth.

Optimum replicability and precision of measurement can be obtained by adjusting the speed of displacement of the electrodes in the conduits with the dynamic of the measurement system. This dynamic in fact differs depending on whether the conductivity of a melted salt is measured (on the order of 1 $\Omega^{-1}$ cm$^{-1}$) or of a liquid metal (on the order of $10^5$ $\Omega^{-1}$ cm$^{-1}$), because the voltage u at the terminals of the cell becomes weaker and weaker for the same current i when the conductivity $\sigma$ increases. To maintain a good signal-to-noise ratio, the integration speed of measurement should be increased, and hence the speed of displacement of the electrodes in the conduits 5 should be decreased. When the frequency f of the measurement current furnished by the generator 22 is increased, it is preferable to reduce the integration time of the measurement.

To monitor the quality of this dynamic relationship between the cell and the measurement chain, the values of the pairs $\Delta R / \Delta l$ are recorded with a similar material having a suitable pass-band.

The optimum is obtained when the traces $\Delta R = f(\Delta l)$ coincide over several cycles, and when the relationship is linear. When these conditions are attained:

a) good measurement of the true conductivity o of the liquid contained in the conduits 5 is attained, as the outcome of the true real value R of the impedance Z, by cutting off all the parasitic impedances, as a result of the motion of the electrodes 6.

b) the signal-to-noise ratio, the criterion of measurement quality, must be high. At the limit, our method of measurement by synchronous analysis is capable of discovering and measuring a signal at a relative level of 1 in a noise level of 300,000.

c) the replicability of the measurement is entirely correct under identical and constant physical and chemical conditions (pressure, temperature, concentration, and purity of the reagents).

As a variant of the mode of signal processing that has just been described, it is possible to simultaneously obtain the values Z (complex impedance), R (pure ohmic resistance), X (reactance) and $\phi$ (phase displacement) as a function of the variation of the frequency f of the measurement current i, without having to re-perform the adjustment of phase and quadrature of the synchronous detectors. To do so, a third synchronous detector 29 is disposed at the terminals of the cell, or in a variant, the synchronous detector 25 is replaced with a double detector. This third detector 29, adjusted in quadrature with the measurement current i, makes it possible to read the voltage Ux in quadrature with the current. By using a second ratiometer 30, the value of the reactants $X = Ux/i$ is obtained directly, and for a given frequency f the value of the complex impedance is deduced: $Z = R + JX$. A third ratiometer (not shown) makes it impossible to obtain the phase displacement tg $\phi$ which is equal to X/R. It is important to stress here that the displacement of the electrodes makes it possible to completely separate the static and dynamic impedances. In effect, they are static impedance $Z = R + JX$ for the cell and the liquid over a length 1, and dynamic impedance, $\Delta Z = \Delta R + J \Delta X$, which is the impedance of the only liquid located in the conduits 5 over $\Delta l$.

If it is now desired to obtain these same values as a function of the frequency, then the current generator 22 is supplemented with a device for varying the frequency as a function of time (31). To avoid having to re-perform the adjustments of the phase of the synchronous detectors when the frequency varies, a fourth synchronous detector 32 is provided, functioning by automatic phase control, which makes it possible to maintain the phase fixing with respect to the current over a very wide range of variation of the frequency f.

As a variant of the mode of signal processing that has just been described, it is possible, with a view to further increasing the quality of the signal-to-noise ratio, to use a method of shifting the measurement signal spectrum toward generally highly elevated frequencies, so as to be able to amplify this signal at a frequency in which the background noise of the entire physical-chemical system is weakest.

To do so, the search for the minimum noise level at the terminals of the call is performed directly by the measuring device within the frequency range used, that is, between 1 Hz and $10^5$ Hz in the absence of the measurement signal i. It is important to recall here that the measurement device known by the term "synchronous analysis" is a true Fourier correlator analyzer, and has the same phase precision as synchronous detection.

In another variant, the solid electrodes 6 may be replaced with coaxial electrodes. By way of non-limiting example, the cell having two conduits and two electrodes becomes a measurement cell with four electrodes.

Advantages: The possibility of increasing i without perturbing the measurement of u brings about a major increase in the signal-to-noise ratio and hence in the measurement power.

In another variant, the current electrodes may be fixed; in this case, they comprise metal cylinders immersed above the calibrated portion of the conduits, while the voltage electrodes are movable and insulated by sheaths of sintered aluminum or some other equivalent insulating material.

In another variant, the cell may also be supplied with a pseudo-random or "noise" signal. In that case, the impedance measurement $Z = R + jX$ is accomplished by RFT (rapid Fourier transform) analysis. This method has the advantage of permitting rapid detection of the electrical characteristics of the cell and of the liquid, within a very wide frequency range. It also makes it possible to obtain the impedance characteristics of the cell in a very global manner, but with low precision.

C - RESULTS

The employment of the method and apparatus that are the subjects of the invention makes it possible to perform measurements of conductivity within a range from $10^{-4}$ to $10^{+6} \Omega^{-1} \cdot cm^{-1}$, and at temperatures from ambient temperature to approximately 1050° C. (with the possibility of extension to cryogenic temperatures and up to 2000° C.). These limits are dictated by the oven technology and the aggressivity of the medium. Replicability and precision can attain $10^{-3}$ of the value measured. This precision requires the use in the measurement chain of equipment (current generators, synchronous detectors, ratiometers) that themselves have proportionate precision. Nevertheless, for industrial measurements that require only low precision (2 to 3%, for example), it is possible to use equipment of lesser precision, while the replicability of the measurements remains nevertheless unchanged.

D - EXAMPLES OF APPLICATIONS

The invention has been employed to study the conductivity of mixtures of metal potassium and potassium chloride, over the entire range of concentration from KCl = 100% to K = 100%, at a pressure of $5.10^5$ Pa, over the entire temperature range from the melting point of potassium (63.5°) to the melting point of potassium chloride (770° C.), and particularly in the vicinity of the zone of immiscibility of the two liquid phases, with a maximum at 790° C. These measurements of conductivity were performed up to 950° C., following the profile of the phase diagram.

Figure 8:
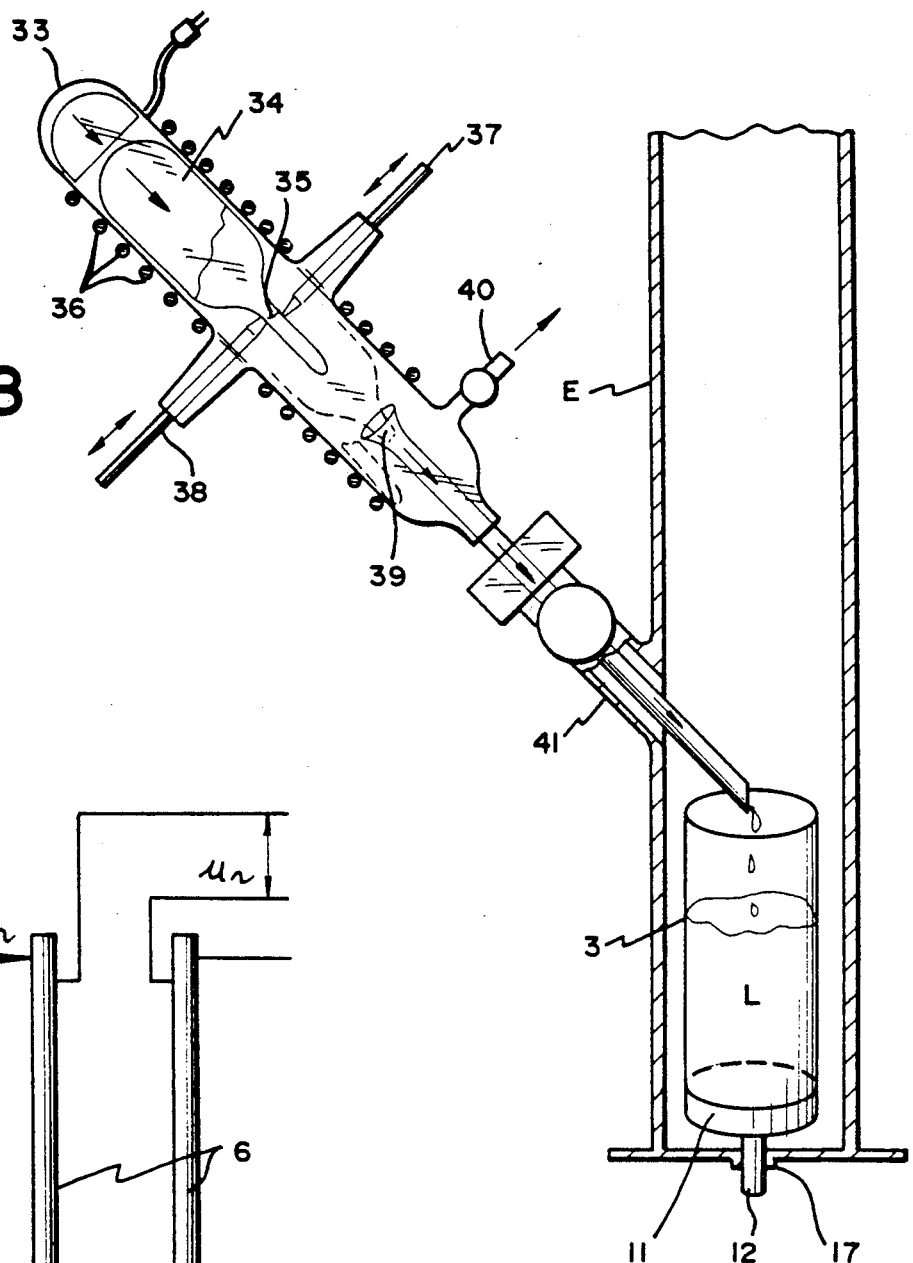
FIG. 8 shows the apparatus with which a highly reactive substance, such as an alkali metal, can be introduced into the crucible outside of contact with air.

The very high reactivity of potassium with air necessitated very special precautions for introducing this metal into the crucible containing the potassium chloride, in argon, by means of lock chamber provided with a novel device, as seen in FIG. 8, making it possible to open the glass ampule containing the potassium in a vacuum and pour it directly into the previously chilled crucible.

This device, which is mounted on a lateral branch conduit 41 of the sealed container E in which the measurement cell is located, includes a glass ampule 33 into which the sealed ampule 34 has been introduced, the neck of which has an incipient fracture 35.

The ampule 33 includes an external electric heating means 36, which makes it possible to bring the potassium to its melting point. Pushing on the rods 37 and 38 makes the print break, and the point drops into the bottom of the ampule, while the liquid potassium drains via the tube 39, the upper end of which is flared, into the crucible 3. A lateral tap 40 makes it possible to create a vacuum in the ampule 33 and then fill it with inert gas. The same device also makes it possible to introduce a salt or any other component into the crucible 3 without its coming into contact with the air.

RESULTS

It has been confirmed that between pure KCl and KCl40/K60 (in moles), the equivalent conductivity $\Lambda$ changes from $10^2$ to $10^5 \Omega^{-1} cm^2$. This is the index of the gradual passage from a complete ionic bond with a coordination number = 6, to an open ionic bond structure with a coordination number = 4. This change in structure is accompanied by the change in slope of the function $d\Lambda/d\Theta$ ($\Lambda$ being expressed as $\Omega^{-1} \cdot cm^2$).

With 60 to 80% K (in moles), the variation of $d\Lambda/d\Theta$ remains low, because the metallic organization of the network is increasingly approached with a structure having a coordination number = 4 (stable tetrahedron). The change in coordination number was determined by neutron diffraction with isotropically substituted mixtures.

Outside this application, the purpose of which was above all to test the method and apparatus under particularly severe conditions, and to verify with precision the theoretical data for mixtures of metals and alkaline salts, the invention has numerous applications in theoretical and industrial electrochemistry.

Among others, the following can be named:

the study of the development of specific impedance of various pyrogenic media (slags or industrial electrolytes) during electrolysis or during a metallurgical process (reduction, refining, etc.). Thus the development of an electrolyte can be tracked without perturbing the process: for example, the cryolithic bath in the tanks for aluminum production by the Hall-Héroult process, or pyrogenic electrolysis. In particular, in tracking the evolution of the impedance of the bath, the appearance of dissolved metal in the electrolyte can be detected and a correlation can be established with the optimal operating conditions.

The dissolution of an oxide in a mixture of molten fluorides can also be tracked, or the attack of a refractory lining by a molten salt or a slag, or the progressive exhaustion in a bath of molten salts of one of its components, such as of NaCl in molten NaCl—$CaCl_2$ baths for the production of sodium by electrolysis.

The fact that the measurements performed according to the invention are not influenced by any of the parasitic signals makes it possible to work in highly perturbed media, where this type of measurement was unattainable by conventional methods; this is the case in industrial electrolysis cells, where the electrical noise level is considerable.

Thus entirely replicable measurement has been possible of the conductivity of cryolith-based electrolysis baths used in industrial cells for the production of aluminum by the Hall-Héroult process. The operating conditions were as follows:

temperature of 960° C. to 1020° C. (constant during the measurement)

bath composition: sodic cryolith $Na_3AlF_6$ with 6% $CaF_2$ and an increasing quantity of $AlF_3$ (respectively, 3, 6 and 9% by weight) added alumina content: from 1 to 9%, by 1% increments.

The values obtained, with precision and replicability on the order of 0.5% relatively, are between 0.300 and 0.500 $\Omega$·cm.

I claim:

1. Device for precise, continuous and dynamic measurement of the electrical resistivity $\sigma$ of a liquid L, at a temperature which may range from low cryogenic temperatures to approximately 2000° C., characterized in that it includes in combination:

a dynamic measurement cell 2 including at least one conduit 5 of electrically insulating material in which a conductive electrode 6 can slide in an alternating periodic motion of amplitude 1, the lower portion of the conduit 5 being calibrated over a length equal to at least 1, and having a cross section s, said cell 2 being immersed in a crucible 3 containing the liquid L at the constant, and adjusted temperature;

a generator 22 of periodic current of frequency f, connected in series with the cell 2 that it supplies at an effective intensity i;

a device 10 for controlling, adjusting and measuring the amplitude of the displacement 1 of each electrode 6;

a means 8 for measuring and adjusting the depth of immersion of each electrode or group of electrode 6 in the liquid L;

a device for adjusting and measuring the speed of displacement $\Delta l/\Delta t$ of the electrode 6 in the conduit 5;

a means of measuring the variation in ohmic resistance R of the cell as a function of the displacement of the electrode 6: $\Delta R/\Delta l$ based on the measurement of the voltage u at the terminals of the cell and of the effective intensity i of the current passing through it, by synchronous, in-phase detection of u and i;

the value of the conductivity o of the liquid L then being equal to:

$$\sigma = \frac{n \cdot \Delta l}{s \cdot \Delta R}$$

where n is the number of electrodes 6 of the cell 2.

2. The device as defined by claim 1, characterized in that it includes at least one means 9 for measuring the temperature at the level of the conduit 5A, in proximity with the interface between the electrode 6 and bath L.

3. The device as defined by claim 2, characterized in that it includes a means for synchronous displacement of the electrode and of the mean 9 for measuring the temperature.

4. The device as defined by claim 1, characterized in that it includes a means for homogenizing the liquid L contained in the crucible 3.

5. The device as defined by claim 4, characterized in that the means for homogenizing the liquid L comprises a means for rotational or translational displacement of the crucible 3, or comprises vibration of said crucible 3.

6. The device as defined by one of claim 1, characterized in that it includes a means 19 for heating the upper portion of the cell, between the upper level of the liquid L and the device 10.

7. The device as defined by claim 6, characterized in that the heating means 19 is divided into a plurality of zones, which are separately supplied with energy and are individually adjustable.

8. The device as defined by one of claims 1–7, characterized in that it includes a single electrode 6 that is movable within the lower portion 5A of a conduit 5, the reverse current toward the generator being assured by a means selected from the group comprising an auxiliary fixed electrode and the use of a crucible 3 of electrically conductive material.

9. The device as defined by one of claims 1–7, characterized in that in a crucible 3, it included two electrodes 6 movable respectively within the lower calibrated portion 5A of two conduits 5 of parallel axes.

10. The device as defined by one of claims 1–7, characterized in that in a crucible 3, it includes two pairs of electrodes 6A–6b, 6C–6D, movable respectively in the calibrated portion 5A of four conduits 5.

11. The device as defined by claim 10, characterized in that the two pairs of electrodes, 6A–6B, 6C–6D and the corresponding conduits 5A each have identical characteristics.

12. The device as defined by claim 10, characterized in that the two pairs of electrodes, 6A–6B, 6C–6D and the corresponding conduits 5A differ among one another by at least one characteristic, selected from the group of characteristics comprising the shape, the diameter of the electrode, the internal diameter of the conduit 5A, and the nature of the conductive material comprising the electrodes.

13. The device as defined by claim 10, characterized in that at least one of the pairs of electrodes has a coaxial structure.

14. The device as defined by claim 1, characterized in that the entire cell is enclosed with a sealed container E, provided with a means of controlled introduction, in an inert gas, of a product that is highly reactive with constituents of the atmosphere.

15. The device as defined by claim 14, characterized in that it includes a branch conduit 43 on the sealed container E, to which is connected, in a sealed manner, an ampule 33 provided with a heating means 36, this ampule including means 37, 38 for releasing the reactive product enclosed in a sealed ampule 34, and means 39 for guiding the liquid or molten reactive product into the crucible 3.

16. A method of precise and continuous measurement of the conductivity of a liquid L at a constant temperature, employing the device that is the subject of claim 1, characterized by the succession of the following operations:

a periodic current of effective intensity i and frequency f is passed into the cell 2, each electrode 6 of which is excited in synchronism in the conduit 5A by a periodic alternating motion of amplitude 1;

the voltage u at the terminals of the cell is measured;

the signals u and i, in phase and in quadrature, are processed by synchronous detection to obtain the value of the pure resistance R of the cell, which is the outcome of the ratio of u and i in phase;

the resistivity o of the liquid L is calculated, using the ratio $\sigma = n \cdot \Delta l / s \cdot \Delta R$, where n is the number of electrodes 6 of the cell, and $\Delta l$ is the amplitude of the motion of the electrode in the conduit 5A.

17. The method as defined by claim 16, characterized in that the speed of displacement of the electrodes 6 in the conduits 5A is adjusted in inverse ratio to the frequency of the generator 22.

18. The method as defined by claim 17, characterized in that this adjustment is performed for a given frequency f, by recording the variation of the function $\Delta l = f(\Delta R)$ and by performing the measurement at the moment when this function is linear, which assures maximum measurement precision.

* * * * *